(12) United States Patent
Argenta

(10) Patent No.: US 7,153,284 B2
(45) Date of Patent: Dec. 26, 2006

(54) USE OF CORRECTIVE INFANT HELMET

(75) Inventor: Louis C. Argenta, Winston-Salem, NC (US)

(73) Assignee: American Southeast Medical Technologies, LLC, Winston-Salem, NC (US)

( * ) Notice: Subject to any disclaimer, the term of this patent is extended or adjusted under 35 U.S.C. 154(b) by 597 days.

(21) Appl. No.: 10/435,781

(22) Filed: May 12, 2003

(65) Prior Publication Data

US 2003/0195450 A1 Oct. 16, 2003

Related U.S. Application Data

(62) Division of application No. 09/479,438, filed on Jan. 7, 2000, now Pat. No. 6,592,536.

(51) Int. Cl.
- A61F 5/00 (2006.01)
- A61F 11/00 (2006.01)
- A61G 15/00 (2006.01)

(52) U.S. Cl. ............... 602/17; 128/845; 128/857

(58) Field of Classification Search ............ 602/1, 602/5, 17, 18; 128/845, 846, 857, 858, 870, 128/871; 2/410, 417–421; 5/636, 655
See application file for complete search history.

(56) References Cited

U.S. PATENT DOCUMENTS

| | | | |
|---|---|---|---|
| 678,417 A | 7/1901 | Muller | |
| 3,957,040 A | 5/1976 | Calabrese | |
| 4,354,283 A | 10/1982 | Gooding | |
| 4,446,576 A | 5/1984 | Hisataka | |
| 4,727,865 A | 3/1988 | Hill-Byrne | |
| 4,776,324 A | 10/1988 | Clarren | |
| 4,845,782 A | 7/1989 | Gregg | |
| 4,979,519 A | 12/1990 | Chavarria et al. | |
| 4,988,093 A | 1/1991 | Forrest, Sr. et al. | |
| 5,075,903 A | 12/1991 | Richoux | |
| 5,094,229 A | 3/1992 | Pomatto et al. | |
| 5,308,312 A * | 5/1994 | Pomatto et al. ............... 602/17 |
| 5,337,420 A | 8/1994 | Haysom et al. | |
| 5,378,042 A | 1/1995 | Daneshvar | |
| 5,511,250 A | 4/1996 | Field et al. | |
| 5,571,220 A | 11/1996 | Hall | |
| 5,637,077 A | 6/1997 | Parker | |

(Continued)

OTHER PUBLICATIONS

Argenta, L. et al., "An Increase In Infant Cranial Deformity With Supine Sleeping Position," *Journal of Craniofacial Surgery*, vol. 7, No. 1, Jan. 1996, pp. 5-11.

(Continued)

*Primary Examiner*—Henry Bennett
*Assistant Examiner*—Kari Petrik
(74) *Attorney, Agent, or Firm*—Kilpatrick Stockton LLP

(57) ABSTRACT

A method and apparatus for treating infant plagiocephaly whereby a helmet encircles the upper cranium of an infant and prevents the infant from resting its head on flattened or depressed regions of the skull. The helmet contemplates an adjustable first member which encircles the infant's upper cranium, and a second member comprising a relatively rigid protruding element that is attached to the exterior surface of the first member. The second member is positioned so that it is superincumbant to flattened or depressed regions, so that when the helmet is worn, the second member forces the infant to rest its head on a different area of the skull, thus passively relieving pressure on the depressed skull, and applying a gentle active pressure to other areas. Additionally, the method an apparatus relates to the treatment of torticollis and other abnormalities of the neck.

19 Claims, 4 Drawing Sheets

U.S. PATENT DOCUMENTS

| | | | |
|---|---|---|---|
| 5,951,503 | A | 9/1999 | Pomatto |
| 6,381,760 | B1 | 5/2002 | Lampe et al. |
| 6,423,019 | B1 * | 7/2002 | Papay et al. ............... 602/17 |
| 6,428,494 | B1 | 8/2002 | Schwenn et al. |
| 6,954,954 | B1 * | 10/2005 | Stelnicki .................. 5/655 |

OTHER PUBLICATIONS

Carson, B. et al., "Technical Strategies: An Assistive Device For The Treatment Of Positional Plagiocephaly," *J. Cranial Facial Surgery*, vol. 11, Mar. 2000, pp. 177-183.

Carson, B. et al., Lambdoid Synostosis and Occipital Plagiocephaly: Clinical Decision Rules For Surgical Interventions. *Neurosurg. Focus*, vol. 2, 1997, pp. 1-5.

Clarren, S, "Plagiocephaly and Torticollis: Etiology, Natural History, and Helmet Treatment," *J. Pediatr.*, vol. 98, Jan. 1981, pp. 92-95.

Danby, P., "Plagiocephaly In Some 10-Year Old Children," *Arch. Dis. Child.*, vol. 37, May 1962, pp. 500-504.

Hellbusch, J. et al., "Active Counter-Positioning Treatment of Deformational Occipital Plagiocephaly," *Nebr. Med. J.*, Dec. 1995, pp. 344-349.

Huang, M. et al., "The Differential Diagnosis of Posterior Plagiocephaly: True Lambdoid Synostosis versus Positional Molding," *Plast. Reconstru. Surg.*, vol. 98, Oct. 1996, pp. 765-774.

Jones, B., "Occipital Plagiocephaly: An Epidemic Of Craniosynostosis," (Editorial) *BMJ*, vol. 315, Sep. 1997, pp. 693-694.

Kaiser, G., The Clinical Significance of Bilateral Synostosis of the Lambdoid Suture and the Usefulness of Its Treatment, "*Child Brain*," vol. 11, 1984, pp. 87-98.

Kane, A. et al., "Observations on a Recent Increase in Plagiocephaly Without Synostosis," *Pediatrics*, vol. 97, Jun. 1996, pp. 877-885.

Moss, S.D., "Nonsurgical, Nonorthotic Treatment of Occipital Plagiocephaly: What is the Natural History of the Misshapen Neonatal Head," *J. Neurosurg*, vol. 87, Nov. 1997, pp. 667-670.

O'Broin, E. et al., "Posterior Plagiocephaly: Proactive Conservative Management," *Br. J. Plas. Surg.*, vol. 52, 1999, pp. 18-23.

Ortega, B., "Some Physicians Do Unnecessary Surgery On Heads Of Infants—They Remold Lopsided Skull When A Corrective Band May Be All That's Needed—At Fault: Sleeping Position," *Wall Street Journal*, Feb. 23, 1996.

Persing, J. (Discussion) "The Differential Diagnosis of Posterior Plagiocephaly: True Lambdoid Synostosis versus Positional Molding," *Plast. Reconstru. Surg.*, vol. 98, Oct. 1996, pp. 775-776.

Pollack, I. et al.,"Diagnosis and Management of Posterior Plagiocephaly," *Pediatrics*, vol. 99, Feb. 1997, pp. 180-185.

Pople, I. et al., "Clinical Presentation and Management of 100 Infants with Occipital Plagiocephaly," *Pediat. Neurosurg.*, vol. 25, 1996, pp. 1-6.

Rekate, H., "Occipital Plagiocephaly: A Critical Review of the Literature," *J. Neurosurg*, vol. 89, Jul. 1998, pp. 24-30.

Ripley, C., "Treatment of Positional Plagiocephaly with Dynamic Orthotic Cranioplasty," *J. Cranial Facial Surgery*, vol. 5, Jul. 1994, pp. 150-159.

Sawin, P. et al., "Quantitative Analysis of Cerebrospinal Fluid Spaces in Children with Occipital Plagiocephaly," *J. Neurosurg.*, vol. 85, Sep. 1996, pp. 428-434.

Danmar Products, Inc., "Special Products for Special Needs", web page at http://danmarproducts.com/index.cfm, as available via the internet and printed Apr. 6, 2005.

* cited by examiner

USE OF CORRECTIVE INFANT HELMET

CROSS-REFERENCE TO RELATED APPLICATIONS

This application is a divisional of U.S. patent application Ser. No. 09/479,438, filed Jan. 7, 2000 now U.S. Pat. No. 6,592,536.

FIELD OF THE INVENTION

The present invention relates to orthopedics, particularly to correcting abnormal head shape in infants, and to the treatment of torticollis.

BACKGROUND

The cranium of a human infant is made up of frontal, parietal, temporal, occipital and other smaller bones that are separated by membranous intervals until brain growth is complete at eighteen to twenty-four months of age. Normally, the infant cranium is symmetrical in shape. However, in the condition known as plagiocephaly, the head is non-symmetrical, becoming parallelogram or rhomboid shaped. Sometimes the plagiocephalic head may correct its shape over time, but often the condition may persist, leading to facial asymmetry with functional, cosmetic, and other disabilities. If orthotic treatment is indicated, it is important to attempt correction of the deformation when the subject is less than a year old, before the sutures in the cranium have solidified.

The shape of the infant cranium is determined by multiple factors including brain growth and development, constraints placed on the skull during and after gestation and bony abnormalities of the skull. When an infant's head is maintained in a nearly fixed position either in utero or when sleeping on a flat surface, the cranium may be progressively deformed. A condition known as occipital positional plagiocephaly or deformational plagiocephaly frequently occurs in children who sleep in a relatively constant position on their backs. For example, as a result of the American College of Pediatrics recommendation that children be placed on their back instead of on their stomach to avoid SIDS (Sudden Infant Death Syndrome), a significant number of new cranial deformities are being seen (Argenta, L. C., et al., *J. Craniofac. Surg.* 7:5–11 (1996)). In addition, many infants have craniums that are deformed either in utero or during the birth process, and sleeping on the depressed portion of the skull accentuates the deformity. Infants who are slower to develop motor activity may also develop cranial abnormalities because of their failure to move their heads frequently. Finally, in some cases plagiocephaly is secondary to synostosis, a condition in which some of the skull sutures fuse too soon, making the skull bulge somewhere else.

Unfortunately, surgery is often the treatment prescribed to correct plagiocephaly of the infant skull. While plagiocephaly secondary to synostosis usually requires surgery, many deformities of the skull can be corrected with appropriate molding helmets (Argenta, L. C., et al., *J. Craniofac. Surg.* 7:5–11 (1996); Claren, S. K., et al., *J. Pediatrics* 94:43–46 (1979)). Such helmets take advantage of the pliability of the infant skull to mold the skull into a normal shape.

There are basically two types of corrective infant helmets. An active helmet is a device that places an active constricting force on the skull to force it to grow in a more normal fashion. These helmets are marketed as Dynamic Orthoplast Cranioplasty (DOC) helmets. In general, active DOC helmets must be custom fitted, require greater amounts of time for fabrication, and must be changed frequently as the infant head increases in size. As a result, DOC helmet therapy requires multiple clinic visits and may cost in the range of several thousands of dollars per patient. In addition, placing a constricting force on the growing brain is not thought to be physiological by most physicians.

Passive helmets or soft shell helmets attempt to take pressure off of the deformed portion of the skull, thus allowing the brain to grow in a more normal fashion. Thus, in contrast to active molding, passive helmets provide for a more gradual and physiological correction of skull shape.

A graded series of sized helmets for treatment of infant plagiocephaly were described in U.S. Pat. No. 4,776,324 to Claren. The Claren helmet is generated based on horizontal and transverse imaging measurements of either a patient skull or the skull of a normal infant. The Claren helmet fully encloses the head, and is designed such that it is slightly larger than the patient's skull. The helmet uses passive molding in that the head grows into the helmet. A graded series of prefabricated helmets are required as an alternative to the previous technology using individualized helmets shaped to each patient's skull.

Although full helmets are effective in treating plagiocephaly (Argenta, L. C., et al., *J. Craniofac. Surg.* 7:5–11 (1996)), they are confining and uncomfortable. Additionally, the use of several helmets is cumbersome and it can be difficult to match the individual patient's skull with the prefabricated helmets available. Alternatively, the helmets which are generated based upon the patient's individualized skull shape are expensive and time consuming to produce.

A cranial remodeling band using active molding to treat plagiocephaly is described in U.S. Pat. No. 5,094,229 to Pomatto. Pomatto described a cranial remodeling band with an internal surface which reflects the desired reconfiguration of the subject's cranium. The technology employs active molding, in that it applies corrective forces to those regions of the cranium which protrude. The technology is expensive, however, in that effective therapy requires that the orthosis be individualized for each subject, and a series of helmets is required for each infant.

A helmet to correct brachycephalic cranial abnormalities is described in U.S. Pat. No. 5,308,312 to Pomatto. The brachycephalic head is expressed as an occipital flattening of the cranium such that the maximal cranial breadth is disproportionately large in relation to the maximum cranial length. The helmet described in U.S. Pat. No. 5,308,312 is designed to address a unique form of abnormal head shape. However, the helmet has many of the disadvantages of other helmets, e.g., for maximum effectiveness, the helmet must be fabricated from an impression of the individual subject's head.

Thus, there is a need to develop corrective infant helmets that provide a gentle but effective therapy for the large majority of plagiocephalic infants. Rather than squeezing unaffected regions of the infant brain, it would be preferable to relieve the pressure from depressed areas of the skull. To enable correction of the abnormality before the brain plates begin to fuse, a helmet must be comfortable enough to be worn for the extended periods of time, up to 23 hours a day. In addition, such therapeutic helmets should be affordable and accessible to the many patients who require treatment.

SUMMARY OF THE INVENTION

The invention provides a helmet which, when worn by an infant, provides for a gentle reshaping of an infant's skull.

The helmet is a band to which a rounded, external protrusion is attached. By positioning the protrusion directly above an area on an infant's head which is abnormally flat, the helmet encourages the infant to roll away from the flattened area, and to rest its head on a different region of the skull. The result is that pressure on the flat area of the skull is reduced, and pressure due to the weight of the infant's head is directed elsewhere. Also, by providing a means for active positioning of the infant's head, the helmet provides a means for treating neck abnormalities such as torticollis.

Thus, the invention provides in one aspect, a method and apparatus for treating plagiocephalic abnormalities of the infant cranium. The invention contemplates a helmet, which when worn by an infant with a plagiocephalic skull, forces the infant to turn his head away from a depressed portion of the skull and to lay upon regions of the head which protrude. In contrast to previous therapeutic methods, the disclosed invention employs both passive and active molding in that it passively relieves pressure from depressed areas of the skull while actively increasing pressure on areas of the skull which are distended.

The helmet comprises a pre-fabricated, adjustable first member that fits around an infant's head, leaving a substantial portion of the patient's upper cranium and ears exposed. In a preferred embodiment the first member comprises two discontinuous sections which overlap each other. The circumference of the first member may be adjusted by sliding the two sections of the first member together or apart. In addition, the first member is punctuated with apertures which provide ventilation, and if required, can be adapted for affixing fasteners. The first member should be strong enough to protect the infant's head, but comfortable to wear. Thus, in a preferred embodiment, the exterior of the helmet comprises a high impact plastic and the interior of the helmet is lined with foam padding.

A substantially rigid convex second member is attached to the exterior of the first member and positioned directly above the depressed region on the infant's skull. The second member is shaped so that when the infant rests it head upon a flat surface, the infant's head rolls off of the second member and comes to rest on a different region of the skull. By adjusting the size and shape of the second member, abnormalities of varying size, shape and location may be selectively treated.

In another aspect, the invention relates to a method for the treatment of torticollis. Placing the second member on the same side of the head as those neck muscles which are affected forces the head to the side away from the torticollis. As the affected muscles become stretched and more relaxed, the second member can be progressively increased in size.

The foregoing focuses on the more important features of the invention in order that the detailed description which follows may be better understood and in order that the present contribution to the art may be better appreciated. There are, of course, additional features of the invention which will be described hereinafter and which will form the subject matter of the claims appended hereto. It is to be understood that the invention is not limited in its application to the details of construction and to the arrangement of the components set forth in the following description and drawings. The invention is capable of other embodiments and of being practiced or carried out in various ways.

From the foregoing summary, it is apparent that an object of the present invention is to provide a new and improved apparatus and method for the treatment of infant head and neck abnormalities. These, together with other objects of the present invention, along with the various features of novelty which characterize the invention, are pointed out with particularity in the claims annexed to and forming a part of this document.

DETAILED DESCRIPTION OF THE INVENTION

Figure 1:
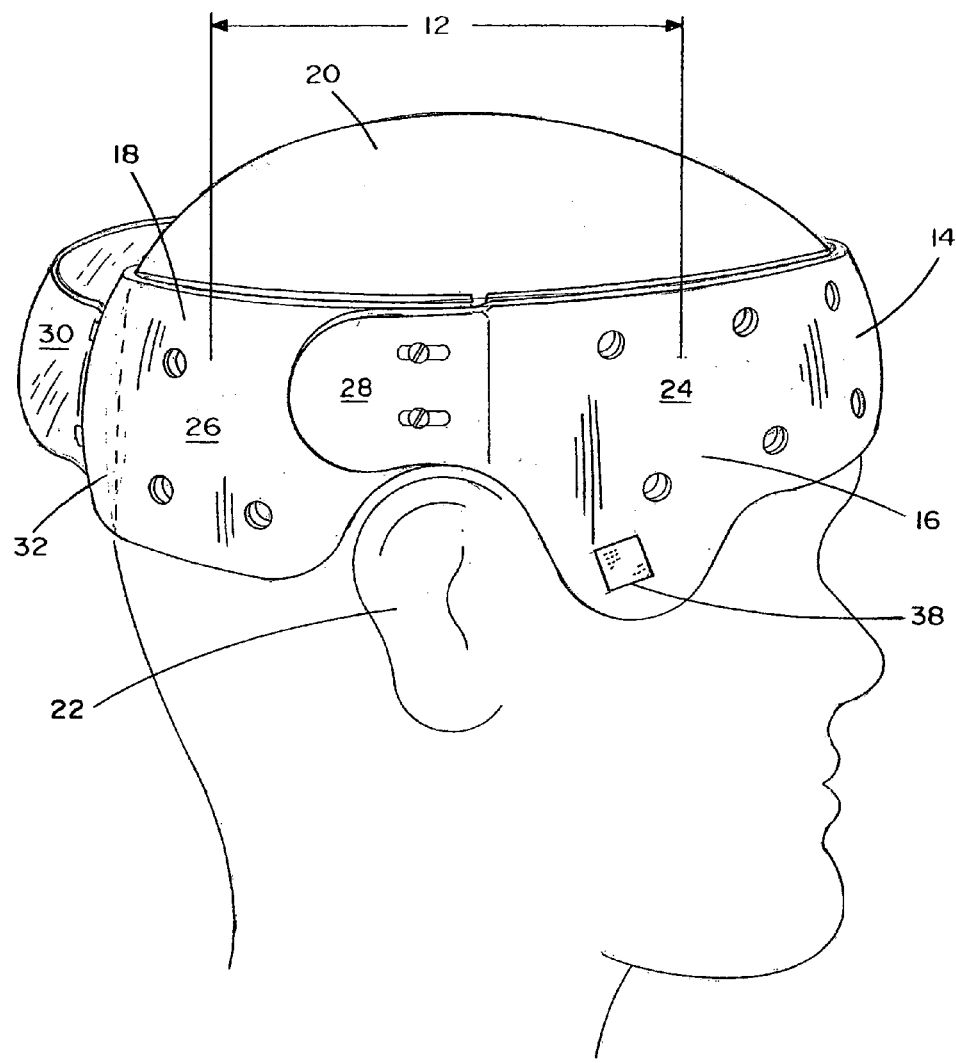
FIG. 1 is a perspective view of an infant wearing the corrective helmet of the invention while lying against a sleeping surface.

According to one aspect of the present invention, an apparatus and a method for treating plagiocephaly and other types of deformational cranial asymmetry in the infant skull comprises an adjustable first member to which is attached a substantially rigid protruding second member, where the first member encircles the cranium of an infant and the second member is positioned above a depressed area on the infant's cranium.

In one embodiment of the invention, the first member encircles substantial areas of the infant's occipital and frontal cranial regions. More preferably, the first member is shaped to provide openings for the infant's cephalad-most cranium and ears. Even more preferably, the first member is comprised of a first section and a discontinuous second section, with guides by which the first and second sections may be overlapped and secured in position relative to one another. The guides preferably comprise oblong-shaped apertures. More preferably, the two sections of the first member are secured relative to one another by means of fasteners which are attached to one of the sections and inserted through guides on the other section. Most preferably, one section of the first member encircles the anterior portion of the infant's cranium and the second section encircles the posterior portion of the infant's cranium. This allows the overlapping segments to be positioned over the infant's ears. The use of an overlapping segment enables the helmet to be decreased or enlarged in size by sliding the two sections of the first member together or apart, respectively. Thus, when initially placed on the infant's head, the helmet is adjusted to fit, and the anterior and posterior bands are positioned by securing fasteners positioned in the overlapping segment. The ability to adjust the size of the helmet minimizes the need for a series of helmets and allows the helmet to accommodate the infant's head as it grows.

The first member should be strong enough to protect the infant's head, but flexible enough for long-term wear. In a preferred embodiment the first member comprises an exterior surface of high impact plastic. Most preferably, the first member comprises an exterior surface of polyethylene. Alternatively, the first member comprises an exterior surface of lightweight metal. More preferably, the first member comprises an exterior surface of aluminum alloy. In another preferred embodiment, the first member comprises an exterior surface selected from the group consisting of polycarbonate, polyethylene, polypropylene, polyamide, polyurethane, cellular plastic, graphite, fiberglass, aluminum, aluminum alloy and titanium.

The interior of the first member comprises foam padding. Most preferably, the interior of the first member comprises open cell polyurethane. In another preferred embodiment, the interior of the first member comprises a material selected from the group consisting of Styrofoam, open cell polyurethane, closed cell polyethylene, and rubber. Alternatively, the interior of the first member comprises an inflatable bladder. If necessary, additional internal padding may be used to enable fitting the helmet an infant whose skull is severely deformed.

A detachable protruding second member is attached to the exterior of the first member and positioned superincumbent to a depressed region on the infant's skull. The protruding second member is a shape such that when the infant rests its head against a flat surface, the protruding second member will encourage the infant's head to roll away from the depressed area, and to lie on a different region of the skull. In a preferred embodiment, the second member is substantially convex curvilinear in shape. Most preferably, the second member comprises a convex band. In another preferred embodiment, the second member comprises a shape selected from the group consisting of a hemisphere, a truncated cone, a trapezoid, and an inverted cup. In another preferred embodiment the second member comprises multiple components that are positioned on the first member to generate a generally hemispherical protrusion. The use of multiple components allows increased variation in the precise shape and size of the protrusion. In yet another preferred embodiment, the second member comprises an inflatable bladder.

The second member may be increased or decreased in size so as to discourage the infant, to varying degrees, from resting on the flat portion of the skull, depending on the severity of the deformity. A larger protrusion would more strongly tend to force the head to the opposite side, whereas a smaller protrusion would simply encourage the head to roll off the affected area. In infants with bilateral deformities, the bump can be applied centrally, thus preventing the infant from lying directly on the central portion of the back of the skull and forcing the head to either side so that corrective growth can occur.

In a preferred embodiment, the first member comprises apertures adapted for affixing fasteners. More preferably, these apertures are positioned at intervals along the first member. The ability to attach fasteners at specified intervals along the first member provides a means by which the second member can be positioned above a depressed region of the infant's skull. Thus, in a preferred embodiment, the second member, or individual sections of the second member, comprise one or more apertures adapted to accommodate fasteners affixed along the first member. More preferably, when the second member is a convex band, the apertures comprise U-shaped slots at the ends of the band. By inserting fasteners affixed at intervals along the first member into apertures in the second member, the second member is secured at various positions along the first member. Additionally, multiple apertures on the first member may be provided to increase ventilation and reduce the overall weight of the helmet.

To increase flexibility in positioning the second member, a method of attaching the second member which is independent of the placement of fasteners on the first member is employed. Thus, in a preferred embodiment, attachment of the second member to the first member comprises a non-invasive method, and more preferably the method is selected from the group comprising adhesive, snaps, VELCRO, and thermal molding.

To force the infant's head away from the underlying depressed region of the skull, the second member should be made of substantially rigid material. This prevents the second member from flexing, thereby preventing the infant from resting its head directly on the second member. Thus, in a preferred embodiment the second member comprises high impact plastic. Most preferably, the second member comprises polyethylene. In another preferred embodiment the second member comprises metal. More preferably, the second member comprises aluminum alloy. In another preferred embodiment, the second member comprises a material selected from the group consisting of polycarbonate, polyethylene, polypropylene, polyurethane, polyamide, cellular plastic, rubber, graphite, fiberglass, aluminum, aluminum alloy, and titanium.

Finally, because the helmet is based on passively relieving pressure on the depressed regions, it does not have to be custom fitted to the infant's skull. Generally, the helmet is adjusted to fit snugly on the infant's head, so that space between helmet and the protruding region(s) on the infant's skull is minimized. However, to secure the helmet in position so that the protruding second member remains over the depressed region of the infant's skull, the helmet is preferably secured on to the infant's head by a detachable chin strap.

In a second aspect of the invention, a method is provided for the treatment of torticollis. Torticollis is a condition in which the muscles of one portion of the neck are excessively tight. Usually the infant favors the affected side of the neck. This results in the head being twisted to one side, which can produce a secondary depression and asymmetry of the skull. Such children require frequent exercises to mobilize the head to the opposite side. The use of a corrective helmet with an appropriate protruding element forces the head to the side away from the torticollis. Progressive increases in size of the protruding element are employed as the neck muscles become increasingly relaxed.

Thus, a typical helmet is constructed of a polyethylene first member approximately 2–4 mm thick and molded to fit on the head of a normal 6 month old infant. The upper opening measures 14 cm across the anterior to posterior axis of the helmet, and 11 cm across the width of the helmet, while the lower opening measures 16.5 cm along the anterior to posterior axis and 13 cm from ear to ear. The first member is formed as two discontinuous sections which overlap as rounded flaps above, and just posterior to, the ears. Oval-shaped guides present on the anterior section of the first member are used to secure both sections relative to one another. These guides are apertures which typically measure on the order of 0.5 cm in width and 2.5 cm in length, and the overlap is secured in place with conventional screws. For comfort, the first member is punctuated with circular apertures 1 cm in diameter which are spaced approximately 2.5 cm apart in a parallelogram pattern. These apertures provide ventilation, and additionally, may be used to position fasteners to attach the second member anywhere along the helmet. Finally, VELCRO strips are glued to the first member to enable attachment of a VELCRO chin strap.

The second member may be of any shape such that when the infant rests its head upon the second member, the head is encouraged to roll to a different area of the skull. Typically, the second member will be formed of polyethylene and is shaped as a convex band. The band measures 16.5 cm by 5 cm, and is shaped so that it protrudes from the first member by a radial distance of about 3–6 cm. The second member is positioned above a depressed region on the infant's skull by inserting fasteners attached to the first member through aperture(s) on the second member. For a second member shaped as a convex band, the apertures are typically U-shaped slots positioned at the end of the band, and the band is secured to the first member using conventional screws.

Referring to FIG. 1, the helmet of this invention takes the form of a first member 12 which is shaped to encircle the frontal 14, temporal 16 and occipital 18 bone regions of the cranium. The helmet leaves a significant part of the infant's head exposed, including the cephalad most cranium 20 and the ears 22. The first member 12 comprises a first section 24 and a second section 26, which are joined at an overlapping section 28. The use of a discontinuous first member enables the helmet size to be increased or decreased to fit around the infant's head. On the back half of the helmet is a detachable protruding second member 30. The second member 30 is positioned on the first member 12 so that the second member 30 is directly overlying a depressed portion of the patient's skull 32. The second member 30 forces the head to lie so that another area of the skull is apposed against a mattress, thus relieving pressure on the depressed side of the skull 32 and applying passive force to a region of the skull which is proportionately distended. A strip of VELCRO 38 is glued to first section 24 to enable the addition of a chin strap for securing first member 12 on the infant's head.

Figure 2:
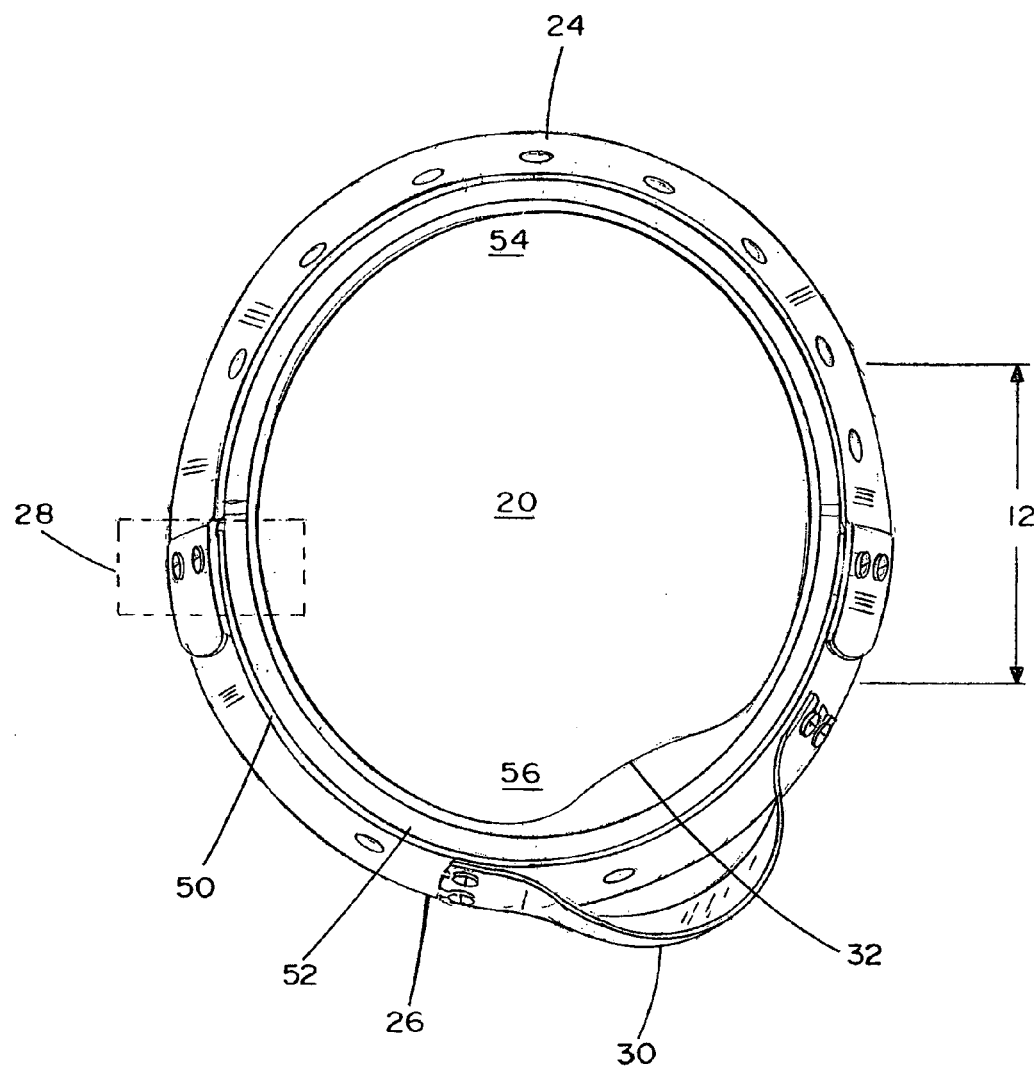
FIG. 2 is a top view of the corrective helmet.

Referring to FIG. 2, the helmet is positioned on the infant's head so that second member 30 overlies a depressed portion of the infant's skull 32. For maximum comfort, the top of the infant's head 20 is exposed. The outer layer 50 of the first member 12 is made of a high impact, light weight material, such as polyethylene. The inner surface of the first member 12 may be lined with a soft cushion 52 such as polyurethane. The first section 24 of the first member 12 which encircles the front of the head 54, and the second section 26 of the first member 12 which encircles the back of the head 56, are fitted such that there is an overlapping section 28. In this mode, the two sections 24 and 26 of the first member 12 can slide towards each other to tighten the helmet, or away from each other to loosen the helmet (see FIG. 3).

Figure 3:
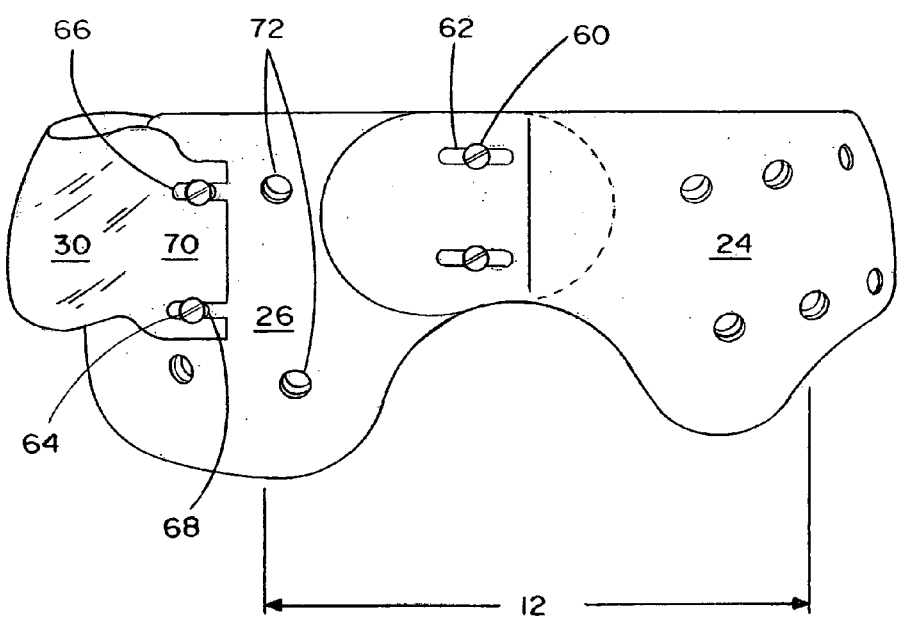
FIG. 3 is a side view of the helmet showing overlap of the anterior and posterior sections of the first member and attachment of the second member.

Referring to FIG. 3, fasteners 60 attached to second section 26 are inserted through guides 62 on first section 24 to stabilize the position of first section 24 and second section 26 relative to each other. The fasteners 60 are then tightened to secure the first member 12 as one continuous unit. Similarly, second member 30 is connected to the second section 26 of first member 12 by fasteners 64 which pass through U-shaped apertures 66 located on the ends 70 of second member 30. Both the second section 26 and the first section 24 of first member 12 are punctuated by apertures 68 to facilitate positioning second member 30 along the helmet. Additional apertures 72 may be added to facilitate cooling of the infant's head, and reduce the overall weight of the helmet.

Figure 4:
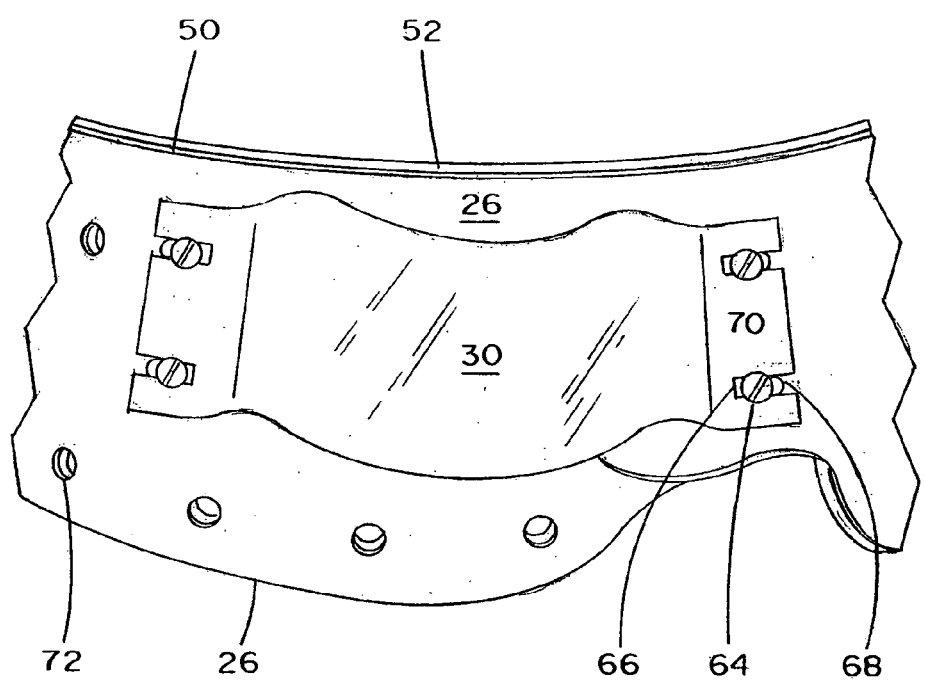
FIG. 4 is a partial side view of the posterior section of the first member and its attachment to the second member.

Referring to FIG. 4, second member 30 is connected to second section 26 of first member 12 by fasteners 64 which pass through U-shaped apertures 66 positioned on the ends 70 of second member 30. Fasteners 64 are then secured in apertures 68 in first member 12. In a preferred embodiment, apertures 68 adapted for affixing second member 30 may be structurally identical to, and therefore co-functional with, apertures 72 adapted for ventilation.

Generally, the benefits of the helmet include a gentle therapy for the treatment of skull abnormalities. The helmet does not squeeze the patient's head, but simply forces the infant to sleep on the non-depressed region of the skull. Except for preventing the infant from lying on the affected area, the helmet allows for universal movement of the head. Because the helmet is open at the top, it is cooler than the available passive helmets which fully enclose the head, allowing for comfortable wear for extended periods. Because the helmet is adjustable and does not require molding to the individual patient head, it eliminates the cost of custom fittings and custom fabrications. In cases where the patient skull is severely deformed, extra foam padding may be placed inside the helmet to facilitate fit.

EXAMPLE

The helmet of the invention is manufactured essentially as follows. To fashion the exterior shell of the first member, two flat, rectangular pieces of plastic are shaped to conform to the overall outline of the first and second sections of the first member, respectively. Both sections of the shell are then molded using a template which has been generated based upon measurements taken from a series of normal infant skulls or CAT skans. After both sections of the shell have hardened into their final shape, padding is glued to the internal surface of each section. The padding does not extend the entire length of each section, but leaves those areas included in the region of overlap uncovered. Multiple apertures are then drilled through both the interior and the exterior of the first member. These apertures are evenly spaced along both sections of the first member. Also, oblong-shaped guide apertures are cut in the overlapping region on one of the sections. Fasteners are then glued onto the external surface, or threaded through the apertures on the first member. Also, VELCRO strips are affixed to the exterior of the helmet to enable the use of a chin strap. The first member is then assembled, leaving fasteners inserted through guides in the overlapping region loose enough to be readjusted.

The template for producing the first member may be produced from any durable material such as wood, plastic or metal. To accommodate changes in the patient's skull size, first members are prefabricated in several sizes such that the resultant helmets encompass the majority of skulls for infants 3 months to 2 years of age. Because infants' skulls follow a bell shaped growth curve, a relatively well-defined and narrow range of helmets will overlap the majority of infant head sizes. Custom helmets can be made for exceptional skulls.

Similarly, a second member shaped as a convex band may be produced by molding the central section of a flat band of plastic around a cylindrical template to produce a convex band. In most cases, a series of three or more bands of increasing convexity are sufficient. Thus, for severe deformities a larger, or more convex, protrusion would be used, while for milder deformities, a smaller protrusion would be used. Alternatively, a substantially hemispherical-shaped mold may be used for making a second member comprised of multiple components. The overall shape of a second member comprised of multiple components may be increased by spacing individual components of the second member further apart, or by using sections which are larger, or more convex, in shape.

With respect to the descriptions set forth above, optimum dimensional relationship of parts of the invention (to include variations in size, materials, shape, form, function and manner of operation, assembly and use) are deemed readily apparent and obvious to those skilled in the art, and all equivalent relationships to those illustrated in the drawings and described in the specification are intended to be encompassed herein. The foregoing is considered as illustrative only of the principal of the invention. Since numerous modifications and changes will readily occur to those skilled in the art, it is not intended to limit the invention to the exact construction and operation shown and described, and all suitable modifications and equivalents falling within the scope of the appended claims are deemed within the present inventive concept.

It is to be further understood that the phraseology and terminology employed herein are for the purpose of description and are not to be regarded as limiting. Those skilled in the art will appreciate that the conception on which this disclosure is based may readily be used as a basis for designing the structures, methods and systems for carrying out the several purposes of the present invention. The claims are regarded as including such equivalent constructions so long as they do not depart from the spirit and scope of the present invention.

What is claimed is:

1. A method for treating infants with skull shape abnormalities comprising the steps of:
   fashioning a first member which comprises an exterior surface and an interior surface to substantially encircle the cranium of an infant,
   attaching to the exterior surface of the first member a second member made of substantially rigid material and comprising a convex curvilinear protrusion; and
   positioning the first member on the infant's head such that the second member is superincumbant to a region on the infant's skull which is abnormally depressed relative to neighboring regions and wherein the second member prevents the infant's head from lying on the first member adjacent to the abnormally depressed region of the infant's skull and encourages the infant's head to lie on other regions of the skull.

2. The method of claim 1, wherein the first member encircles substantial areas of the infant's occipital and frontal cranial regions.

3. The method of claim 1, wherein the first member comprises at least one opening for the infant's cephaladmost cranium.

4. The method of claim 1, wherein the first member comprises openings for the infant's ears.

5. The method of claim 1, wherein the first member comprises a first section and a second section.

6. The method of claim 5, wherein the first section of the first member overlaps the second section of the first member to allow the first member to be enlarged or decreased in circumference.

7. The method of claim 6, wherein one section of the first member comprises fasteners which are inserted through apertures in the other section of the first member thereby securing the first section and the second section of the first member in a stable position relative to one another.

8. The method of claim 1, wherein the exterior surface of the first member comprises high impact plastic.

9. The method of claim 8, wherein the exterior surface of the first member comprises polycarbonate, polyethylene, polypropylene, polyamide, cellular plastic, or fiberglass.

10. The method of claim 1, wherein the interior surface of the first member comprises padding.

11. The method of claim 10, wherein the padding comprises foam, open cell polyurethane foam, closed cell polyethylene foam, or rubber.

12. The method of claim 1, wherein the first member comprises one or more apertures adapted for affixing the second member to the first member.

13. The method of claim 12, wherein the one or more apertures are positioned at intervals along the first member.

14. The method of claim 1, wherein the second member comprises non-invasive attachment to the first member.

15. The method of claim 14, wherein the non-invasive attachment comprises adhesive, snaps, hook and loop fasteners, or thermal molding.

16. The method of claim 1, wherein the second member comprises a hemisphere, a truncated cone, an inverted cup, or a convex band.

17. The method of claim 1, wherein the second member comprises high impact plastic.

18. The method of claim 17, wherein the second member comprises polycarbonate, polyethylene, polypropylene, polyurethane, polyamide, cellular plastic, rubber, or fiberglass.

19. The method of claim 1, wherein the first member is held in position on the infant's head by a chin strap.

* * * * *

UNITED STATES PATENT AND TRADEMARK OFFICE
CERTIFICATE OF CORRECTION

| | | |
|---|---|---|
| PATENT NO. | : 7,153,284 B2 | Page 1 of 1 |
| APPLICATION NO. | : 10/435781 | |
| DATED | : December 26, 2006 | |
| INVENTOR(S) | : Louis C. Argenta | |

It is certified that error appears in the above-identified patent and that said Letters Patent is hereby corrected as shown below:

Column 1, Line 34, the phrase "placed on the skull during and after gestation and bony" should read -- placed on the skull during and after gestation, and bony --

Column 5, Line 9, the phrase "used to enable fitting the helmet an infant" should read -- used to enable fitting the helmet to an infant --

Signed and Sealed this

Twenty-first Day of August, 2007

JON W. DUDAS
*Director of the United States Patent and Trademark Office*